United States Patent
Huber et al.

(10) Patent No.: US 9,969,969 B2
(45) Date of Patent: May 15, 2018

(54) **FED-BATCH FERMENTATION PROCESS AND CULTURE MEDIUM FOR THE PRODUCTION OF PLASMID DNA IN *E. COLI* ON A MANUFACTURING SCALE**

(75) Inventors: Hans Huber, Vienna (AT); Gerhard Weigl, Amstetten (AT); Wolfgang Buchinger, Vienna (AT)

(73) Assignee: BOEHRINGER INGELHEIM RCV GMBH & CO KG, Vienna (AT)

( * ) Notice: Subject to any disclaimer, the term of this patent is extended or adjusted under 35 U.S.C. 154(b) by 1008 days.

(21) Appl. No.: 12/388,848

(22) Filed: Feb. 19, 2009

(65) Prior Publication Data
US 2009/0253182 A1 Oct. 8, 2009

Related U.S. Application Data

(63) Continuation of application No. 11/101,764, filed on Apr. 8, 2005, now abandoned.

(60) Provisional application No. 60/568,857, filed on May 7, 2004.

(30) Foreign Application Priority Data

Apr. 8, 2004 (EP) ..................................... 04008556

(51) Int. Cl.
*C12P 19/34* (2006.01)
*C12N 1/20* (2006.01)
*C12N 15/10* (2006.01)

(52) U.S. Cl.
CPC ........... *C12N 1/20* (2013.01); *C12N 15/1003* (2013.01); *C12P 19/34* (2013.01)

(58) Field of Classification Search
CPC ..... C12P 19/34; C12N 15/1003; C12N 15/70; C12N 1/20; C07K 16/32; C07K 2317/515; C07K 2317/76; C07K 2317/77; C07K 2317/92; G01N 2333/485; G01N 2333/71; G01N 2800/52; G01N 2800/54; G01N 2800/56
See application file for complete search history.

(56) References Cited

U.S. PATENT DOCUMENTS

| | | | |
|---|---|---|---|
| 5,130,415 A * | 7/1992 | Tecce et al. | 530/324 |
| 5,487,986 A | 1/1996 | Wan et al. | |
| 5,534,421 A * | 7/1996 | Livshits et al. | 435/116 |
| 5,955,323 A | 9/1999 | Chen | |
| 5,981,735 A | 11/1999 | Thatcher et al. | |
| 6,255,099 B1 | 7/2001 | Duttweiler et al. | |
| 6,664,078 B1 * | 12/2003 | Schmidt et al. | 435/91.1 |
| 8,048,651 B2 * | 11/2011 | Zelder et al. | 435/115 |
| 2004/0002081 A1 | 1/2004 | Urthaler et al. | |
| 2005/0170404 A1 * | 8/2005 | Cho et al. | 435/6 |
| 2005/0233365 A1 | 10/2005 | Huber et al. | |

FOREIGN PATENT DOCUMENTS

| | | |
|---|---|---|
| DE | 101 06 493 A1 | 8/2002 |
| DE | 10106493 A1 | 8/2002 |
| GB | 1 442 715 A1 | 1/1974 |
| GB | 1442715 A | 7/1976 |
| WO | 96/40905 A1 | 12/1996 |
| WO | 9640905 A1 | 12/1996 |
| WO | WO 9640905 A1 * | 12/1996 |
| WO | 99/61633 A2 | 12/1999 |
| WO | 9961633 A2 | 12/1999 |
| WO | 02/064752 A1 | 8/2002 |
| WO | 20020064752 A1 | 8/2002 |

OTHER PUBLICATIONS

Chen et al. (1997) J. Industrial Microbiol and Biotechnol. 18: 43-48.*
Lahijani et al. (1996) Juman Gene Therapy 7: 1971-1980.*
Richaud et al. (1987) J. Bacteriol. 169(4): 1454-1459.*
O'Kennedy et al. (2000) Journal of Biotechnology 76: 175-173.*
Rothen et al. (1998) Bioengineering 58: 92-100.*
Schleef et al. (2002) Eng. Life Sci. 2, 6: 158-160.*
Kozlov Y I et al; Cloning of Threonine Operon Genes in *Escherichia coli*; Genetika (1980) vol. 16 No. 1 pp. 66-77.
Roya Lahijani et al; High-Yield Production of pBR322-Derived Plasmids Intended for Human Gene Therapy by Employing a Temperature-Controllable Point Mutation; Human Gene Therapy (1996) vol. 7 No. 7 pp. 1971-1980; Mary Ann Liebert, Inc.
Tamio Mizukami et al; Essential Role of Aspartokinase in L-Threonine Production by *Escherichia coli* W Mutants; Agricultural and Biological Chemistry (1986) vol. 50 No. 4 pp. 1015-1018.
Ronan D. O'Kennedy et al; Effects of Fermentation Strategy on the Characteristics of Plasmid DNA Production; Biotechnology and Applied Biochemistry (2003) vol. 37 No. 1 pp. 83-90; Portland Press Ltd.
Sandrine Petry et al; Factors Affecting Exocellular Polysaccharide Production by *Lactobacillus delbrueckii* Subsp. *bulgaricus* Grown in a Chemically Defined Medium; Applied and Environmental Microbiology (2000) vol. 66 No. 8 pp. 3427-3431.
Herve Robert et al; Glycine Betaine, Carnitine, and Choline Enhance Salinity Tolerance and Prevent the Accumulation of Sodium to a Level Inhibiting Growth of Tetragenococcus Halophila; Applied and Environmental Microbiology (2000) vol. 66 No. 2 pp. 509-517.
Julia Soutourina et al; Role of D-Cysteine Desulfhydrase in the Adaptation of *Escherichia coli* to D-Cysteine; The Journal of Biological Chemistry (2001) vol. 276 No. 44 pp. 40864-40872.
Xia Dongxiang et al; Effect of L-Isoleucine and Glycine on Catechol 2, 3-dioxygenase Expression and Excretion in *Escherichia coli*; (1994) vol. 34 No. 1 pp. 37-44.

(Continued)

*Primary Examiner* — Lisa J Hobbs
(74) *Attorney, Agent, or Firm* — Marc A. Began; Atabak R. Royaee; Edouard G. Lebel (57) ABSTRACT

A process for producing plasmid DNA *E. coli* cells comprises a pre-culture and fed-batch process. The culture media of the batch phase and the culture medium added during the feeding phase are chemically defined. The culture medium of the feeding phase contains a growth-limiting substrate and is added, for at least a fraction of the feeding phase, at a feeding rate that follows a pre-defined exponential function, thereby controlling the specific growth rate at a pre-defined value. The process results in high yield and homogeneity of plasmid DNA.

26 Claims, 6 Drawing Sheets

(56) References Cited

OTHER PUBLICATIONS

Xiao-Ming Yang et al; Production of recombinant Human Interferon-Alpha-1 by *Escherichia coli* Using a Computer-Controlled Cultivation Process; Journal of Biotechnology (1992) vol. 23 No. 3 pp. 291-301; Elsevier Science Publishers.
Erik R. Zinser et al; Mutations Enhancing Amino Acid Catabolism Confer a Growth Advantage in Stationary Phase; Journal of Bacteriology (1999) vol. 181 No. 18 pp. 5800-5807.
Dana C. Andersen et al; Metabolic Oscillations in an *E. coli* Fermentation; Biotechnology and Bioengineering (2001) vol. 75 No. 2 pp. 212-218; John Wiley & Sons, Inc.
W. Chen et al; Automated Fed-Batch Fermentation with Feed-Back Controls Based on Dissolved Oxygen (DO) and pH for Production of DNA Vaccines; Journal of Industrial Microbiology and Biotechnology (1997) vol. 18 pp. 43-48.
Yasuji Furutani et al; Cloning and Sequencing of the cDNA for Human Monocyte Chemotactic and Activating Factor (MCAF); Biochemical and Biophysical Research Communications (1989) vol. 159 No. 1 pp. 249-255; Academic Press, Inc.
Robert P. Lawther et al; Molecular Basis of Valine resistance in *Escherichia coli* K-12; Proceedings of the National Academy of Sciences of the United States of America (1981) vol. 78 No. 2 pp. 922-925.
R.D. O'Kennedy et al; Effects of Growth Medium Selection on Plasmid DNA Production and Initial Processing Steps; Journal of Biotechnology (2000) vol. 76 pp. 175-183; Elsevier Science.
Jeffrey B. Ulmer et al; Toward the Development of DNA Vaccines; Current Opinion in Biotechnology (1986) vol. 7 pp. 653-658; Current Biology Ltd.
Tom Schoenfeld et al; Effects of Bacterial Strains Carrying the endA1 Genotype on DNA Quality Isolated with Wizard(TM) Plasmid Purification Systems; Promega Notes Magazine (1995) vol. 53 pp. 12-22.
Jeffrey Vieira et al; The pUC Plasmids, an M13mp7-Derived System for Insertion Mutagenesis and Sequencing with Synthetic Universal Primers; Gene (1982) vol. 19 pp. 259-268; Elsevier Biomedical Press.
Zhijun Wang et al; Medium Design for Plasmid DNA Production Based on Stoichiometric Model; Process Biochemistry (2001) vol. 36 pp. 1085-1093.
Celeste Yanisch-Perron et al; Improved M13 Phase Cloning Vectors and Host Strains: Nucleotide of the M13mp18 and pUC19 Vectors; Gene (1985) vol. 33 pp. 103-119; Elsevier Science Publishers.
J. Zhang et al; Chemically Defined Media for Commercial Fermentations; Applied Microbiology Biotechnology (1999) vol. 51 pp. 407-421; Springer-Verlag.
Carsten Voss et al; Production of Supercoiled Multimeric Plasmid DNA for Biopharmaceutical Application; Journal of Biotechnology (2003) vol. 105 pp. 205-213.
Richard E. Herman et al; Cloning and Expression of the Beta-D Galactosidase Gene from *Streptococcus-thermophilus* in *Escherichia-coli*; Applied and environmental Microbiology (1986) vol. 52 No. 1 pp. 45-50.
Ross H. Durland et al; Manufacturing and Quality Control of Plasmid-Based Gene Expression Systems; Advanced Drug Delivery Reviews (1998) vol. 30 pp. 33-48; Elsevier Science.
Haruo Ikeda et al; Organization of the Biosynthetic Gene Cluster for the Polyketide Anthelmintic Macrolide Avermectin in Steptomyces Avermitilis; Proceedings of the National Academy of Sciences of the United States of America (1999) vol. 96 pp. 9509-9514.
Satoshi Omura et al; Genome Sequence of an industrial Microorganism Streptomyces Avermitilis: Deducing the Ability of Producing Secondary Metabolites; Proceedings of the National Academy of Sciences of the United States of America (2001) vol. 98 No. 21 pp. 12215-12220.
Ulrich Riegert et al; Distal Cleavage of 3-Chlorocatechol by an Extradiol Dioxygenase to 3-Chloro-2-Hydroxymuconic Semialdehyde; Journal of Bacteriology (1998) vol. 180 No. 11 pp. 2849-2853.
F. Soubrier et al; pCOR: A New Design of Plasmid Vectors for Nonviral Gene Therapy; Gene Therapy (1999) vol. 6 pp. 1482-1488; Stockton Press.
H.C. Birnboim et al; A Rapid Alkaline Extraction Procedure for Screening recombinant plasmid-DNA; Nucleic Acids Research (1979) vol. 7 No. 6 pp. 1513-1523.
Kirill A. Datsenko et al; One-Step Inactivation of Chromosomal Genes in *Escherichia coli* K-12 Using PCR Products; PNAS (2000) vol. 97 No. 12 pp. 6640-6645.
Robin G. Taylor et al; *E.coli* Host Strains Significantly Affect the Quality of Small Scale Plasmid DNA Preparations Used for Sequencing; Nucleic Acids Research (1993) vol. 21 No. 7 pp. 1677-1678; Oxford University Press.
Catherine Richaud et al; molecular cloning, characterization, and Chromosomal Localization of dapF, the *Escherichia coli* gene for Diaminopimelate Epimerase; Journal of Bacteriology (1987) vol. 169 No. 4 pp. 1454-1459.
Martin Schleef et al; 20 Issues of Large-Scale Plasmid DNA Manufacturing; In Biotechnology (1999) 2nd ed. vol. 5a pp. 443-469; Wiley-VCH, Weinheim.
CBER, Center for Biologics Evaluation and Research; Guidance for Industry: Guidance for Human Somatic Cell Therapy and Gene Therapy (1998) i-27.
Martin Schleef et al; Plasmid DNA for Pharmaceutical Applications; Developments in Biologicals (2000) vol. 104 pp. 25-31.
P. Reinikainen et al; *Escherichia coli* Plasmid Production in Fermenter; Biotechnology and Bioengineering (1989) vol. 33 pp. 386-393; John Wiley & Sons, Inc.
K. H. Hofmann et al; Amplification of pBR322 Plasmid DNA in *Escherichia coli* relA Strains During Batch and Fed-Batch Fermentation; Journal Basic Microbiology (1990) vol. 30 No. 1 pp. 37-4.
WHO: World Health Organization; Guidelines for Assuring the Quality of DNA Vaccines; Technical Report Series (1998) No. 878 pp. 77-88.
Hizuko Kakinuma et al; Cloning of Large DNA Fragments, which Hybridize with Actinorhodin Biosynthesis Genes, from Kalafungin and Nanaomycin a Methyl Ester Producers and Identification of Genes for Kalafungin Biosynthesis of the Kalafungin Producer; The Journal of Antibiotics (1991) vol. 44 No. 9 pp. 995-1005.
Borys Wrobel et al; Replication Regulation of ColE1-Like Plasmids in Amino Acid-Starved *Escherichia coli*; Plasmid (1998) vol. 39 pp. 48-62; Academic Press.
Tove Atlung et al; Role of the Rom Protein in Copy Number Control of Plasmid pBR322 at Different Growth Rates in *Escherichia coli* K-12; Plasmid (1999) vol. 41 pp. 110-119; Academic Press.
Joseph Sambrook et al; Molecular Cloning: A Laboratory Manual, 3rd ed, (2001) vol. 1 pp. iv-xx; Cold Spring Harbor Laboratory Press.
EMEA: The European Agency for the Evaluation of Medicinal Products; Note for Guidance on the Quality, Preclinical Aspects of Gene Transfer Medicinal Products (2001) pp. 1-30.
International Search Report for PCT/EP2005/003599 dated Aug. 25, 2005.
Anderson, Dana C. et al. "Metabolic Oscillations in an *E. coli* Fermentation" (2001) Biotechnology and Bioengineering, vol. 75, No. 2, pp. 212-218.
Atlung, Tove et al. "Role of the Rom Protein in Copy Number Control of Plasmid pBR322 at Different Growth Rates in *Escherichia coli* K-12" (1999) Plasmid, vol. 41, pp. 110-119.
Birnboim, H.C. et al. "A rapid alkaline extraction procedure for screening recombinant plasmid DNA" (1979) Nucleic Acids Research, vol. 7, No. 6, pp. 1513-1523.
CBER, Center for Biologics Evaluation and Research, U.S. Food and Drug Administration, (1998) Guidance for Industry, Guidance for Human Somatic Cell Therapy and Gene Therapy, 30 pgs.
Chen, W. et al. "Automated fed-batch fermentation with feed-back controls based on dissolved oxygen (DO) and pH for production of DNA vaccines" (1997) Journal of Industrial Microbiology & Biotechnology vol. 18, pp. 43-48.
Datsenko, Kirill A. et al. "One-step inactivation of chromosomal genes in *Escherichia coli* K-12 using PCR products" (2000) PNAS, vol. 97, No. 12, pp. 6640-6645.

(56) References Cited

OTHER PUBLICATIONS

Dongxiang, Xia et al. "Effect of L-Isoleucine and Glycine on Catechol 2,3-Dioxygenase Expression and Excretion in *Escherichia coli*" (1994) Weishengwu Xuebao, vol. 34, No. 1 pp. 37-44 (English Abstract included).
Durland, Ross H. et al. "Manufacturing and quality control of plasmid-based gene expression systems" (1998) Advanced Drug Delivery Reviews, vol. 30, pp. 33-48.
Furutani, Yasugi et al. "Cloning and Sequencing of the cDNA for Human Monocyte Chemotactic and Activating Factor (MCAF)" (1989) Biochemical and Biophysical Research Communications, vol. 159, No. 1, pp. 249-255.
Herman, Richard E. et al. "Cloning and Expression of the β-D-Galactosidase Gene from *Steptococcus thermophilus* in *Escherichia coli*" (1986) Applied and Environmental Microbiology, vol. 52, No. 1, pp. 45-50.
Hofmann, K.H. et al. "Amplification of pBR322 plasmid DNA in *Escherichia coli* relA strains during batch and fed-batch fermentation" (1990) J. Basic Microbiol. 30, 1, pp. 37-41.
Ikeda, Haruo et al. "Organization of the biosynthetic gene cluster for the polyketide anthelmintic macrolide avermectin in Streptomyces avermitilis" (1999) Proc. Natl. Acad. Sci., vol. 96, pp. 9509-9514.
Kakinuma, Shizuko et al. "Cloning of Large DNA Fragments, which Hybridize with Actinorhodin Biosynthesis Genes, From Kalafungin and Nanaomycin a Methyl Ester Producers and Identification of Genes for Kalafungin Bioysnthesis of the Kalafungin Producer" (1991) The Journal of Antibiotics, vol. 44, No. 9, pp. 995-1005.
Kozlov, Yu. I. et al. "Cloning of Threonine Operon Genes in *Escherichia coli*" (1980) Genetika Moscow, vol. 16, No. 1, XP008050284, pp. 66-77. (English Abstract included).
Lahijani, Roya et al. "High-Yield Production of pBR322-Derived Plasmids Intended for Human Gene Therapy by Employing a Temperature-Controllable Point Mutation" (1996) Human Gene Therapy, vol. 7, pp. 1971-1980.
Lawther, Robert P. et al. "Molecular basis of valine resistance in *Escherichia coli* K-12" (1981) Proc. Natl. Acad. Sci., vol. 78, No. 2, pp. 922-925.
Mizukami, Tamio et al. "Essential Role of Aspartokinase in L-Threonine Production by *Escherichia coli* W Mutants" (1986) Agricultural and Biological Chemistry, vol. 50, Issue 4, pp. 1015-1018.
O'Kennedy, Ronan D. et al. "Effects of fermentation strategy on the characteristics of plasmid DNA production" (2003) Biotechnology and Applied Biochemistry, vol. 37, pp. 83-90.
Omura, Satoshi, et al. "Genome sequence of an industrial microorganism Streptomyces avermitilis: Deducing the ability of producing secondary metabolites" (2001) PNAS, vol. 98, No. 21, pp. 12215-12220.
Paalme, T et al. Glucose-Limited Fed-Batch Cultivation of *Escherichia coli* with Computer-Controlled Fixed Growth Rate (1990) Biotechnology and Bioengineering, vol. 35, pp. 312-319.
Petry, Sandrine et al. "Factors Affecting Exocellular Polysaccharide Production by *Lactobacillus delbrueckii* subsp. *bulgaricus* Grown in a Chemically Defined Medium" (2000) Applied and Environmental Microbiology, vol. 66, No. 8, pp. 3427-3431.
Reinikainen, P. et al. "*Escherichia coli* Plasmid Production in Fermenter" (1989) Biotechnology and Bioengineering, vol. 33, pp. 386-393.
Richaud, Catherine et al. "Molecular Cloning, Characterization, and Chromosomal Localization of dapF, the *Escherichia coli* Gene for Diaminopimelate Epimerase" (1987) Journal of Bacteriology, vol. 169, No. 4, pp. 1454-1459.
Riegert, Ulrich et al. "Distal Cleavage of 3-Chlorocatechol by an Extradiol Dioxygenase to 3-Chloro-2-Hydroxymuconic Semialdehyde" (1998) Journal of Bacteriology, vol. 180, No. 11, pp. 2849-2853.
Robert, Herve et al. "Glycine Betaine Carnitine and Choline Enhance Salinity Tolerance and Prevent the Accumulation of Sodium to a Level Inhibiting Growth of Tetragenococcus halophila" (2000) Applied and Envimomental Microbiology, vol. 66, No. 2, pp. 509-517.
Sambrook, Joseph et al. "Molecular Cloning, a Laboratory Manual" 3rd Edition, (2001) Cold Springs Harbor Laboratory Press, 17 pgs.
Schleef, M. et al. "Plasmid DNA for Pharmaceutical Applications" (2000) Dev. Biol. vol. 104, pp. 25-31.
Schoenfeld, Tom et al. "Effects of Bacterial Strains Carrying the endA1 Genotype on DNA Quality Isolated with Wizard (TM) Plasmid Purification Systems" (1995) Promega Notes Magazine, No. 53, 12, 8 pgs.
Soubrier, F. et al. "pCOR: a new design of plasmid vectors for nonviral gene therapy" (1999) Gene Therapy, vol. 6, pp. 1482-1488.
Soutourina, Julie et al. "Role of D-Cysteine Desulfhydrase in the Adaptation of *Escherichia coli* to D-Cysteine" (2001) The Journal of Biological Chemistry, vol. 276, Issue 11/2, pp. 40864-40872.
Taylor, Robin G. et al. "*E. coli* host strains significantly affect the quality of small scale plasmid DNA preparations used for sequencing" (1993) Nucleic Acids Research, vol. 21, No. 7, pp. 1677-1678.
Ulmer, Jeffrey B. et al. "Toward the development of DNA vaccines" (1996) Current Opinion in Biotechnology, vol. 7, pp. 653-658.
Vieira, Jeffrey et al. "The pUC plasmids, an M13mp7-derived system for insertion mutagenesis and sequencing with synthetic universal primers" (1982) Gene, vol. 19, pp. 259-268.
Voss, Carsten, et al. "Production of supercoiled multimeric plasmid DNA for biopharmaceutical application" (2003) Journal of Biotechnology, vol. 105, pp. 205-213.
Wang, Zhijun et al. "Medium design for plasmid DNA production based on stoichiometric model" (2001) Process Biochemistry, vol. 36, pp. 1085-1093.
World Health Organization, "Annex 3, Guidelines for assuring the quality of DNA vaccines" (1998) WHO Technical Report Series No. 878. 14 pgs.
Wrobel, Borys et al. "Replication Regulation of ColE1-like Plasmids in Amino Acid-Starved *Escherichia coli*" (1998) Plasmid, vol. 39, pp. 48-62.
Yang, Xiao-Ming et al. "Production of recombinant human interferon-a1 by *Escherichia coil* using a computer-controlled cultivation process" (1992) Journal of Biotechnology, vol. 23, pp. 291-301.
Yanisch-Perron, Celeste et al. "Improved M13 phage cloning vectors and host strains: nucleotide sequences of the M13mp18 and pUC19 vectors" (1985) Gene, vol. 33, pp. 103-119.
Zhang, J et al. "Chemically defined media for commerical fermentations" (1999) Appl. Microbiol Biotechnol., vol. 51, pp. 407-421.
Zinser, Erik R. et al. "Mutations Enhancing Amino Acid Catabolism Confer a Growth Advantage in Stationary Phase" (1999) Journal of Bacteriology, vol. 181, No. 18, pp. 5800-5807.

* cited by examiner

FED-BATCH FERMENTATION PROCESS AND CULTURE MEDIUM FOR THE PRODUCTION OF PLASMID DNA IN E. COLI ON A MANUFACTURING SCALE

RELATED APPLICATIONS

This Application is a continuation of U.S. Ser. No. 11/101,764, filed Apr. 8, 2005, now abandoned, which claims priority benefit from U.S. Provisional 60/568,857, filed May 7, 2004 and from EP 04 008 556.5, filed Apr. 8, 2004, each of which is hereby incorporated by reference in its entirety.

FIELD OF THE INVENTION

The invention relates to the fermentation of *Escherichia coli* for the production of plasmid DNA (pDNA), in particular for pDNA intended for the use in gene therapy and DNA vaccination.

INTRODUCTION

The requirement for industrial fermentation of pDNA came up by the clinical success of gene therapy and DNA vaccination during the last decade.

Gene therapy is the treatment or prevention of disease by the administration, delivery and expression of genes in mammalian cells. The ultimate goal of gene therapy is to cure both inherited and acquired disorders by adding, correcting, or replacing genes. Basically, there are two types of gene therapy vectors to achieve these goals, i.e. viral vectors based on inactivated viruses and non-viral vectors based on plasmid DNA. The present invention relates to the production of non-viral plasmid DNA.

Since it was demonstrated that intramuscular injection of pDNA encoding an antigen elicits both a humoral and a cellular immune response, naked plasmid DNA has become of particular importance.

The desired efficiency of a fermentation process for manufacturing plasmid DNA is characterized by a high yield of pDNA, either per volume fermentation broth (volumetric yield) or per biomass aliquot (specific yield). In the meaning of the present invention, yield is the concentration of plasmid DNA per volume or cell weight. Beyond a high yield, the plasmid has to be present in its intact covalently closed circular (ccc) or supercoiled form. In the meaning of the invention, the percentage of ccc form is termed "plasmid homogeneity". The concentration of other plasmid forms such as open circular (oc), linear and dimeric or multimeric forms, should be reduced to a minimum in the purified plasmid bulk, and are consequently not desired during fermentation.

Therapeutic plasmids consist of three essential parts, i.e. the therapeutic gene (the "gene of interest") under the control of a eukaryotic promoter, mostly the cytomegalovirus (CMV) promoter, an origin of replication (ori) for the autonomous propagation in the prokaryotic cell, and a selection marker, usually an antibiotic resistance gene. While the therapeutic gene is of clinical and medicinal relevance, both the or/and the selection marker play a crucial role during plasmid production, especially during fermentation. For construction of a therapeutic plasmid, a key factor is the choice of an origin of replication that replicates to a high number of plasmid copies per cell. Most therapeutic vectors bear the ColE1-type ori. Plasmids having a ColE1 origin derived from pBR322 may reach copy numbers of 50-100 plasmids per cell, plasmids derived from pUC can reach copy numbers of several hundred.

The antibiotic selection marker and the use of antibiotics are necessary during transformation and selection of plasmid harboring cells. However, antibiotic selection pressure should be avoided during industrial manufacturing. It is therefore desirable to develop fermentation processes allowing a stable propagation of the vector without plasmid loss.

The choice of the bacterial host strain is another important factor to be considered for fermentation of pDNA. Desirable host phenotypes include those with the ability to grow to a high cell density, to achieve high plasmid copy numbers, to generate a minimum of plasmid-free cells, to have a minimum potential for genetic alterations of the plasmid, the production of plasmids being predominantly supercoiled, and the compatibility with common purification procedures. Most strains of *E. coli* can be used to propagate pDNA, although the strain may have an effect on the quantity and quality of the obtained pDNA (Schoenfeld et al., 1995). Currently there is no consensus on the genotypic or phenotypic characteristics that would be ideal for bacterial strains used for pDNA manufacture. Frequently, the strain DH5-alpha was used before for fermentation of pDNA.

BACKGROUND OF THE INVENTION

A number of approaches have been described for fermentation of pDNA. The proposed methods differ with regard to the level of control imposed upon the cells and the numerous factors that influence fermentation. Low-level control simply allows plasmid-bearing cells to grow, whereas high-level tightly-controlled fermentations reach high yields of pDNA by specific measures which enhance replication.

For pDNA production on a laboratory scale, cultivation of plasmid-bearing cells in shake flasks is the simplest method, which however normally achieves low yields. Plasmid yields obtained from shake flask cultivations are in the range of 1.5 to 7 mg per L culture broth (O'Kennedy et al., 2003; Reinikainen et al., 1988; O'Kennedy et al., 2000). In shake flask cultivations, several drawbacks such as poor oxygen transfer and the lack of possibility for pH value control, limit the pDNA yield. In U.S. Pat. No. 6,255,099 it was shown that, even in shake flask cultivations, a pDNA yield of up to 109 mg/L can be achieved with certain medium compositions and buffering conditions.

To obtain higher quantities of plasmids, it has been suggested to cultivate the cells in controlled fermenters. A simple fermentation method, in which all nutrients are provided from the beginning and in which no nutrients are added during cultivation, is termed "batch-cultivation" or "batch fermentation". The application of batch processes in controlled fermenters has led to an increase of pDNA yield per volume. Depending on the plasmid/host combination and on the culture medium, the yield of pDNA obtained from such batch fermentations can vary strongly. Typical plasmid yields reported are in the range between 3.5 and 50 mg/L (O'Kennedy et al., 2003; WO 96/40905; U.S. Pat. No. 5,487,986; WO 02/064752; Lahijani et al., 1996). These cultivations were carried out with culture media containing so-called "complex components" as carbon and nitrogen sources. These components are obtained from biological sources; they include e.g. yeast extract, soy peptone or casein hydrolysate.

Culture media consisting exclusively or predominantly of complex components are termed "complex media". Media that are composed of both a defined portion (defined carbon source, salts, trace elements, vitamins) and a complex portion (nitrogen source), are termed "semi-defined" media. According to U.S. Pat. No. 5,487,986, a very high amount of various complex components (50 g/L in total) was used.

Culture media containing complex components have the disadvantage that these components originate from biological materials; therefore, the composition of the medium underlies normal natural deviations that make the cultivation process less reproducible. The same applies when a manufacturer changes the production process or when there is a change of supplier. Further disadvantages of using complex medium components are the uncertainty about the exact composition (presence of undesired substances), the impossibility to do stoichiometric yield calculations, the formation of undesired products upon sterilization, difficult handling due to poor dissolution, formation of dust as well as clumping during medium preparation. During fermentation, complex media more readily tend to foaming. Complex components of animal origin (meat extracts, casein hydrolysates) are in particular undesired for pDNA production due to the risk of transmissible spongiform encephalopathy and their use is therefore restricted by pharmaceutical authorities (CBER 1998).

Because of the drawbacks of complex medium components, media have been developed that do not contain any complex components. Such culture media, which are termed "defined" or "synthetic" media, are composed exclusively of chemically defined substances, i.e. carbon sources such as glucose or glycerol, salts, vitamins, and, in view of a possible strain auxotrophy, specific amino acids or other substances such as thiamine. Chemically defined media have the advantage that their composition is exactly known. This allows better process analysis, fermentation monitoring and the specific addition of particular substances which enhance growth or product formation. The well-known composition allows to set up mass balance calculations, which facilitate the prediction of growth and the identification of possibly lacking nutrients. Compared to complex media, fermentations with defined media show enhanced process consistency and improved results during scale-up. Further practical aspects of defined media are better solubility, the absence of inhibiting by-products upon sterilization, and less foam formation during cultivation (Zhang and Greasham, 1999).

Synthetic media, that were not specifically developed for pDNA production, such as M9 (Sambrook and Russel, 2001), may result in a low pDNA yield (WO 02/064752). In batch fermentations with defined culture media that were specifically designed for pDNA production, a higher yield of pDNA was obtained (Wang et al., 2001; WO 02/064752). The latter demonstrated that pDNA homogeneity was more than 90% ccc form. The enhanced yields of pDNA according to WO 02/064752 and Wang et al. (2001) were achieved by supplementation of amino acids that are biosynthetic building blocks of nucleosides, or by the direct addition of nucleosides.

Although batch fermentations are usually simple and short, they have fundamental disadvantages that result in limited plasmid DNA yields. This is due to substrate inhibition and salt precipitation at high nutrient concentrations in the batch medium. Furthermore, the growth rate in batch fermentations cannot be controlled directly; it is therefore unlimited, while steadily changing during fermentation, and ceases only when one or more nutrients are depleted or if metabolic by-products (such as acetate) inhibit growth of the cells.

Consequently, in order to increase biomass and plasmid yield in pDNA production, fed-batch fermentations have been developed. A fed-batch fermentation is a process in which, after a batch phase, a feeding phase takes place in which one or more nutrients are supplied to the culture by feeding.

Different strategies have been pursued for fed-batch fermentation of E. coli to produce plasmid DNA:

One method is the application of a feed-back control algorithm by feeding nutrients in order to control a process parameter at a defined set point. Feed-back control is hence directly related to cell activities throughout fermentation. Control parameters which have been used for feed-back control of fermentations include pH value, on-line measured cell density or dissolved oxygen tension (DOT). These methods have the benefit that high biomass concentrations can be obtained with a reduced risk of overfeeding the culture with the fed nutrient.

For pDNA fermentation, a feed-back algorithm for controlling the dissolved oxygen tension at a defined set point by the feeding rate was used (WO 99/61633). When applying another, more complex algorithm, both the DOT and the pH were used as control parameters for a feed-back cultivation method (U.S. Pat. No. 5,955,323; Chen et al., 1997). In that method, the DOT was controlled by the agitation rate and feeding of a concentrated complex medium (glucose, yeast extract), whereby the pH was concomitantly maintained with ammonium hydroxide.

The application of feed-back algorithms is accompanied by a number of disadvantages. One is, that the feeding rate depends on current process parameters such as the DOT. Irritation of the process due to whatever reason may influence the control parameter and has therefore an impact on the feeding rate and consequently on growth and pDNA yield. For instance, when an antifoam agent has to be added, the DOT changes (normally decreases), which results in a lower feeding rate. This makes the fermentation process less reproducible. Further difficulties arise during scale-up of the process, since fermenters of different geometry or size show different oxygen transfer rates. Since the oxygen transfer rate is coupled to the DOT, the feed-back controlled feeding rates of fermenters of varying size will differ, and therefore the process will not be directly scaleable.

Another disadvantage of feed-back control is that the specific growth rate can not be exactly predefined nor controlled, resulting in suboptimal yields in processes, where the product formation is dependent on growth. However, for pDNA fermentation, a strong dependence of the volumetric and specific plasmid yield on the specific growth rate was shown (WO 96/40905; O'Kennedy et al., 2003).

Control of the specific growth rate can be achieved by another fundamental feeding mode based on the supply of feed medium following an exponential function. The feeding rate is controlled based on a desired specific growth rate P. When a defined medium is applied, growth can be exactly predicted and pre-defined by the calculation of a biomass aliquot X to be formed based on the substrate unit S provided (under consideration of the biomass yield coefficient $Y_{X/S}$).

The invention described in WO 96/40905 uses an exponential fed-batch process for plasmid DNA production and obtains a high yield of biomass (50 g DCW, dry cell weight per L), but reaches a low pDNA yield (18 mg/L; 0.36 mg/g dry cell weight). In another example for exponential feeding, a plasmid yield of 30 mg/L and 6 mg/g DCW was achieved (O'Kennedy et al., 2003). A higher pDNA yield of 220 mg/L was obtained by Lahijani et al. (1996) by combining exponential feeding with temperature-controllable enhancement of plasmid replication. In these examples of exponential feeding, only O'Kennedy et al. (2003) gave details on pDNA homogeneity, which was 50-70% ccc form. Currently, all exponential fed-batch processes, use complex components in both the batch medium and the feed medium.

In summary, the current state of the art in fermentation for manufacturing therapeutic plasmid DNA can be characterized as follows:

Batch fermentations that are widely applied for pDNA production are associated with technological and economical drawbacks. For batch fermentations, complex or semi-defined media are mostly used, resulting in a pDNA yield that ranges between 3.5 and 68 mg per L culture broth. Fed-batch processes that apply feed-back control either use semi-defined media or a complex pre-culture medium followed by a defined medium in the main culture. With feed-back algorithms, plasmid yields between 100 and 230 mg/L can be obtained. Exponentially fed fermentations use semi-defined culture media. The plasmid yield of exponential fermentations is in a broad range between 18 and 220 mg/L. In general, many pDNA fermentation processes suffer from poor homogeneity (i.e. percentage of supercoiled plasmid). Exceptions are fermentations that use a defined medium in the main culture, where a percentage of ccc form over 90% can be obtained.

BRIEF DESCRIPTION OF THE INVENTION

The present invention relates to a process for producing plasmid DNA on a manufacturing scale, wherein *E. coli* cells that bear a plasmid carrying a gene of interest are first grown in a pre-culture and subsequently fermented in a main culture, wherein the main culture is a fed-batch process comprising a batch phase and a feeding phase. The culture medium of the batch phase and the culture medium added during the feeding phase are chemically defined, and the culture medium of the feeding phase is added, at least for a fraction of the feeding phase, at a feeding rate that follows a pre-defined exponential function, thereby maintaining the specific growth rate at a pre-defined value.

In the meaning of the present invention, the term "defined medium" refers to a medium that is exclusively composed of chemically defined single components.

In a preferred embodiment, the fraction of the feeding phase during which addition of the feed medium follows the exponential function is such that more than 20% of the total dry cell weight to be obtained in the feeding phase is generated during said fraction of the feeding phase.

In a preferred embodiment, all media, including the medium used in the pre-culture, are chemically defined.

In the process of the invention, any strain of *E. coli* may be used. Host strains useful in the invention may have any genotype; preferred host strains have mutations in the genes relA, endA, and recA. A the most preferred embodiment of the invention, the *E. coli* strain K12 JM108 or a derivative thereof is used.

In the process of the invention, any plasmid that can replicate autonomously in *E. coli* can be used. Preferred plasmids have a ColE1-type origin of replication, most preferably a replicon derived from a pUC plasmid (originally described by Vieira and Messing, 1982, Yanisch-Perron et al. 1985).

In the process of the invention, the medium of the batch phase and the medium of the feeding phase are chemically defined, preferably, all cultivation media, including the one used in the pre-culture, are chemically defined, which means they do not contain any complex medium components. The culture media used in the process of the invention contain an organic carbon source, preferably glucose, and one or more inorganic nitrogen sources like ammonium salts. Further components are inorganic salts containing macro and micro elements. In case the strain is auxotrophic for a specific nutrient, e.g. a vitamin like thiamine or an amino acid such as proline, these substances are also present in the medium.

Preferably, the culture media of the invention are free of antibiotics as normally used for imposing a selection pressure on plasmid-bearing cells.

In a preferred embodiment of the invention, the culture medium contains, independent of a possible amino acid auxtotrophy, isoleucine. This means that isoleucine may be present also when a strain is not auxotrophic for isoleucine. In the case that a strain does have an isoleucine auxotrophy, isoleucine is preferably present in a concentration that exceeds the amount necessary for complementing said auxotrophy.

The growth rate—and thus the feeding rate by which the growth rate is maintained—may have any value that ensures growth of the cells and plasmid replication.

It has surprisingly been found that the method of the invention results in a pDNA yield of more than 600 mg/L and a specific pDNA yield of up to 45 mg/g dry cell weight, whereby a pDNA homogeneity of more than 90% ccc can be reached.

In a preferred embodiment, high-copy-number plasmids (e.g. derived from pUC) are used in fermentations that are operated at low specific growth rates.

In fermentations operated at low growth rates, due to amino acid starvation, uncharged tRNAs arise which increase the plasmid copy number. When re/A-negative *E. coli* strains are used, the cells cannot respond to amino acid starvation in terms of metabolic down-regulation, consequently plasmid replication is enhanced. The additional supply with isoleucine supports the disturbance of the amino acid metabolism and increases the pDNA yield even further.

It has been surprisingly found that the process of the invention results in an outstandingly high specific and volumetric yield of plasmid DNA, accompanied by a high homogeneity of the pDNA throughout the fermentation time.

DETAILED DESCRIPTION OF THE INVENTION

Host Strain

In the method of the invention, any strain of *E. coli* may be used that can be cultivated in a defined medium. Preferably, a strain derived from K-12 is used. The selection of an appropriate host strain may be based on the host's genotype, i.e. the specific mutations characterizing the strain, and/or on systematic comparison of several strains in experimental fermentations.

In a preferred embodiment of the invention, the strain has a mutation in the relA gene. This gene is responsible for the synthesis of guanosine tetraphosphate (ppGpp), a signal molecule which triggers the so-called "stringent response" in the cell upon amino acid limitation. In relA+ strains, amino acid limitation leads to a down-regulation of essential metabolic pathways involved in DNA replication and transcription (Wrobel and Wergrzyn, 1998). Strains having a mutation in the relA gene therefore continue to grow and to replicate plasmids upon amino acid limitation, which has been shown to be an important prerequisite for growing cells in a chemically defined medium with high plasmid replication rates (Hofmann et al., 1989).

In a further preferred embodiment of the invention, host strains having, in addition to a relA mutation, mutations in the genes of endA (endonuclease A) and of recA (recombination system) are used, since these mutations increase the structural integrity of the plasmid.

Examples for suitable host strains are DH1, DH5, DH5-alpha, DH10B, JM108, JM109 and HB101.

In the method of the invention, the most preferred *E. coli* K-12 strain is JM108 (ATCC No. 47107; DSMZ No. 5585; genotype: F$^-$, recA1, endA1, gyrA96, thi-1, hsdR-17, supE44, relA1, λ$^-$ and Δ(lac-proAB); Yanisch-Perron et al., 1985) or a JM108 derivative that has been obtained by genetic manipulation of JM108. During host screening in experimental fermentations done in preliminary tests leading to the present invention, JM108 showed consistently the highest pDNA yield (both volumetric and specific).

Plasmids

The method of the invention can be used for the manufacture of any plasmid that is capable of autonomous replication in *E. coli*, irrespective of the replication origin, and irrespective of the intended use, e.g. as a gene therapy vector or a vector to be used as a DNA vaccine. Suitable plasmids are, for example derived from pBR322, pUC18, pUC19, pcDNA3 (Invitrogen).

In a preferred embodiment of the invention, a plasmid having a ColE1-type origin of replication is used. The rationale behind this is that upon amino acid limitation, transfer RNAs (tRNAs) which are not charged with amino acids, arise. These uncharged tRNAs interact with the ColE1 replication origin in a way that leads to an enhanced replication rate of the plasmid. This effect is stronger when a re/A− strain is used (Wrobel and Wergrzyn, 1998).

In a particularly preferred embodiment of the invention, a ColE1-derived plasmid of the pUC type (Vieira and Messing, 1982; Yanisch-Perron et al., 1985) is used. The pUC plasmids have a mutation in the copy number-decreasing protein Rom and achieve therefore a higher plasmid copy number than the normal ColE1-type plasmids. Since the replication-enhancing effect of rom-plasmids was especially shown at low specific growth rates (Atlung et al., 1999), the combination of pUC plasmids with a low growth rate cultivation is preferred in the method of the invention.

Defined Culture Medium

A chemically defined culture medium is used during the batch phase and the feeding phase of the main culture, preferably also in the pre-culture. Thus, in a preferred embodiment, no complex components are applied throughout the entire fermentation process.

Furthermore, in a preferred embodiment, no antibiotics for selection of plasmid-bearing cells are used throughout the main culture. Preferably, also the medium used in the pre-culture is free of antibiotics.

The culture medium used in the pre-culture and in the main culture may have identical or different composition.

An organic carbon source is used in the pre-culture, in the batch medium, and in the feed medium. The carbon source may be selected from glucose, fructose, lactose, sucrose, arabinose, glycerol or any other carbon source that can be metabolized by *E. coli* as well as mixtures of different carbon sources. Preferably, the carbon source is glucose.

The carbon source used in the different phases of the process and in the feed medium may be identical or different. Usually the carbon source in the medium of the pre-culture and the batch medium of the main culture are identical, preferably, the same carbon source is also contained in the feed medium.

In the batch medium, the concentration of the carbon source may range between ca. 1 and ca. 100 g/L, preferably ca. 10 to ca. 30 g/L. The concentration of the carbon source may be the same in the pre-culture and in the batch medium of the main culture.

In the feeding phase, it is the carbon source of the feed medium that preferably serves as the limiting substrate to control the specific growth rate. In the most simple variant of the process, the feed medium contains only the carbon source.

The concentration range of the carbon source in the feed medium is between ca. 100 and ca. 750 g/L. In case glycerol is used, the concentration of glycerol may range from 100 to 1000 g/L in the feed medium. Preferably, the carbon source is glucose, which is present in the feed medium in a concentration between ca. 300 to ca. 500 g/L.

In a preferred embodiment of the invention, the feed medium contains the growth limiting carbon source and, in addition, some or all medium components that are additionally present in the batch medium.

According to the invention, ammonium salts or ammonium hydroxide are preferably used to serve as initial nitrogen source in the pre-culture and in the batch medium. Usually, ammonium chloride is used, but also ammonium sulfate, ammonium carbonate, ammonium phosphate or ammonium hydroxide or any other ammonium salt are suitable. The concentration of the nitrogen source may be chosen such that the ammonium concentration is in the range of ca. 0.1 to ca. 8 g $NH_4$ per L, preferably, the ammonium concentration is ca. 0.5 to ca. 2 g/L, most preferably it is ca. 0.6 g/L.

In a preferred embodiment, a solution of ammonium hydroxide is supplied separately throughout the entire main culture both for control of the pH value and for continuous supply with nitrogen, both during the batch phase and the feeding phase. This has the advantage that not all the ammonium is provided in the initial batch medium, which may have a toxic effect on the culture. In this preferred embodiment, the ammonium concentration in the medium remains essentially constant throughout the fermentation. Control of the pH value with ammonium hydroxide is further more beneficial as compared to the use of sodium hydroxide or potassium hydroxide, because it is not associated with the accumulation of sodium and potassium ions in the medium, which may cause osmotic stress and thus inhibit the culture. Since the supply with ammonium hydroxide is independent of the feed, it is not growth rate limiting and not part of the feeding algorithm. The concentration of the ammonium solution may be between ca. 5 and ca. 40% m/m ammonium.

It may be necessary, in the case of an amino acid auxotrophy of the host strain, that the medium contains, in addition, one or more of the relevant amino acids. when, according to a preferred embodiment, the host strain is JM108 is used, which requires for its growth the amino acid proline, the use of proline in the culture media is essential. It is further essential that the auxotrophic amino acids are also present in the feed medium. In the case that such amino acids are present in the feed solution, they neither serve as rate limiting factors to control the growth rate, nor are they intended to enhance plasmid replication. The concentration range of the auxotrophic amino acids may be chosen between ca. 0.05 to ca. 2 g/L and is preferably ca. 0.2 g/L.

In a preferred embodiment of the invention, the culture medium contains, independent of a possible amino acid auxotrophy of the host, the amino acid isoleucine, which is present in the medium of the batch culture and preferably also in the feed medium. Optionally, isoleucine is also present in the pre-culture medium. *E. coli* K-12 strains have a mutation of a gene involved in the biosynthesis of isoleucine. This results in the repression of isoleucine biosynthesis when isoleucine is absent and when, at the same time, valine is present (Lawther et al., 1981). Consequently, valine is toxic for isoleucine-starved cells. Interaction with the isoleucine metabolism by valine was found even upon intracellular generation of valine, but this effect was abolished by supply of isoleucine (Andersen et al., 2001). In the course of the experiments that have led to the present invention, the toxicity of valine was confirmed. It was further found that although the culture could grow in the defined medium without isoleucine, the supply with isoleucine increased the yield of plasmid DNA significantly. The presence of isoleucine in the defined medium is therefore an essential feature in a preferred embodiment of the invention. The concentration range of isoleucine may be chosen between ca. 0.05 to ca. 2 g/L and is preferably ca. 0.1 to ca. 0.3 g/L, most preferably ca. 0.2 g/L.

In addition, the culture medium contains inorganic salts which serve as a supply with macro elements and micro elements (trace elements), and, optionally organic substances that positively effect the metabolism of the cells, e.g. citric acid. In case of auxotrophies other than for amino acids, e.g. vitamins, the relevant substances are additionally included in the culture medium. In the embodiment of the invention which uses the host strain JM108, thiamine has to be present in the culture medium. Thiamine is preferably present in a concentration between ca. 0.1 and ca. 100 mg/L, most preferably in a concentration of about 1 mg/L.

Magnesium is usually supplied in the form of $MgSO_4*7H_2O$, however, other magnesium salts are equally suitable. The concentration of the magnesium salt(s) is usually between ca. 0.1 and ca. 5 g/L and is preferably ca. 0.25 g/L.

Phosphorus is preferably supplied in the form of $KH_2PO_4$ and/or $Na_2HPO_4*12H_2O$, but also other phosphorus salts such as $K_2HPO_4$, $NaH_2PO_2$, $Na_2HPO_4$, $NH_4H_2PO_4$ and/or $(NH_4)_2HPO_4$ may be used. The concentration of the phosphorus salt(s) may be between ca 0.5 to ca. 25 g/L, preferably ca. 2.0 to ca. 15 g/L, most preferably ca. 5.0 g/L $KH_2PO_4$ or ca. 14.0 g/L $Na_2HPO_4*12H_2O$, respectively.

Elements like calcium, iron, cobalt, manganese, copper and zinc are usually present in the culture media as follows: $CaCl_2*2H_2O$ in the range between ca. 1 and ca. 20, preferably ca. 7.5 mg/L; $FeSO_4*7H_2O$ in the range between ca. 1 and ca. 20, preferably ca. 5.5 mg/L; $COCl_2*6H_2O$ in the range between ca. 0.5 and ca. 10, preferably ca. 2.5 mg/L; $MnSO_4*H_2O$ in the range between ca. 0.1 and ca. 5, preferably ca. 2.0 mg/L, $CuSO_4*5H_2O$ in the range between ca. 0.05 and ca. 2, preferably ca. 0.25 mg/L, and $ZnSO_4*7H_2O$ in the range between ca. 0.05 and ca. 2, preferably ca. 0.3 mg/L. Any other salt containing the respective element can be used in the respective concentration ranges.

The above-defined medium components and their concentrations refer to the medium used in the batch culture. Usually, the concentration of the nutrients in the feed medium, except for the nitrogen source (which is added separately during the feeding phase) is ca. 2-fold to ca. 100-fold higher as compared to the batch medium.

As a minimum requirement, the feed medium contains the substrate, usually the carbon source, in an amount that is growth limiting. In addition to the limiting carbon source, the feed medium may contain some or all medium components that are present in the batch medium, or, albeit this is less preferred, the feed medium may contain equivalent components, e.g. different salts of the same elements.

By way of example, the composition of the feed medium is as following: glucose 300 g/L; $MgSO_4*7H_2O$ 7.2 g/L; L-proline 6 g/L; L-isoleucine 6 g/L; thiamine hydrochloride 30 mg/L, citric acid 2 g/L; $KH_2PO_4$ 5.4 g/L; $Na_2HPO_4*12H_2O$ 14.4 g/L; $CaCl_2*2H_2O$ 220 mg/L; $FeSO_4*7H_2O$ 170 mg/L; $COCl_2*6H_2O$ 72 mg/L, $MnSO_4*H_2O$ 51 mg/L, $CUSO_4*5H_2O$ 8 mg/L and $ZnSO_4*7H_2O$ 9 mg/L.

In a further aspect, the present invention relates to a culture medium for producing plasmid DNA in *E. coli* on a manufacturing scale. The medium is a chemically defined medium that contains a) an organic carbon source selected from glucose, glycerol, fructose, lactose, sucrose, arabinose, or a mixture thereof;

b) an inorganic nitrogen source selected from ammonium salts and ammonium hydroxide, wherein the nitrogen source is present as a component of the medium and/or or added to the medium during fermentation;

c) inorganic ions that serve as a supply with macro and micro elements;

d) optionally one or more substances that complement an auxotrophy of the *E. coli* strain, and e) isoleucine.

The culture medium of the invention is useful in the batch phase and/or the feeding phase of the method of the invention or as a medium in any other method for cultivating Ecolifor producing plasmid DNA on a manufacturing scale, i.e. for fermentation of *E. coli* in any batch or fed-batch culture.

In a further embodiment, the medium of the invention is a batch medium that is present at the start of a batch fermentation or at the start of the batch phase of a fed-batch fermentation and contains a) glucose in concentration of ca. 10 to ca. 30 g/L;

b) an ammonium salt or ammonium hydroxide in a concentration such that the ammonium concentration is ca. 0.5 to ca. 2 g/L;

c) inorganic ions that serve as a supply with macro and micro elements;

d) optionally one or more substances that complement an auxotrophy of the *E. coli* strain; and e) isoleucine in a concentration of ca. 0.1 to ca. 0.3 g/L.

In another embodiment, the medium of the invention is a feed medium that is added during the feeding phase of a fed-batch fermentation and contains
 a) glucose in concentration of ca. 300 to ca. 500 g/L;
 b) inorganic ions that serve to supply with macro and micro elements;
 c) optionally one or more substances that complement an auxotrophy of the *E. coli* strain; and
 d) isoleucine in a concentration of ca. 6 g/L.

Exponential Feeding Procedure

According to the invention, addition of culture medium ("feed medium") during at least a fraction of the feeding phase is done by following an exponential function in order to allow the culture to grow at any desired, pre-defined specific growth rate μ.

In its most general definition, the exponential function may be defined by the equation $V_t = \text{const}*e^{\mu t}$ or $F_t = \text{const}*e^{\mu t}$, respectively. This equation also encompasses a function $V_t = \text{const}*e^{\mu t}+A$ or $F_t = \text{const}*e^{\mu t}+A$, wherein A is a value that can vary within a wide range that depends on the scale of fermentation. Preferably, A=0. Values A≠0 result in an function that is shifted upwards (A>0) or downwards (A>0) as compared to a function wherein A=0.

In a preferred embodiment of the invention the function for defining the mode for adding the feed medium is as follows:

$$V_t = \frac{X_0}{Y_{X/S}*C_S}*e^{\mu t}.$$

In this function, $V_t$ is the volume [L] of the feed medium to be added at the time interval t [h] calculated from the start of the feed. $X_0$ is the total amount of biomass dry cell weight [g] at the time point of start feed. $Y_{X/S}$ is the biomass yield coefficient (g dry cell weight per g substrate) and $C_S$ is the concentration of the growth-limiting substrate (usually an organic carbon source) in the feed medium [g/L].

The function for defining the feeding mode can also be characterized by the flow rate of the feed medium:

$$F_t = \frac{\mu*X_0}{Y_{X/S}*C_S}*e^{\mu t}.$$

In this function, $F_t$ is the flow rate [L/h] of the feed medium to be added at the time point t [h] calculated from the start of the feed.

The specific growth rate μ [h$^{-1}$] can be chosen at any desired pre-determined value and/or as determined to be optimal in previous fermentations or based the results of experimental fermentations. The biomass yield coefficient can be taken from the literature or determined in preliminary cultivation experiments. The amount of biomass at the start of feeding $X_0$ can be determined by measuring the optical density or by taking a value of previous experiments or by calculation of the theoretical value via the initial substrate concentration in the batch medium and the biomass yield coefficient.

The characteristic feature of such a feeding mode is that the feeding profile, which follows an equation as given above, exclusively depends on the period of time between the start of feeding and a given point of time. With such a feeding profile, the specific growth rate can be pre-defined at any desired value.

The time point for starting the feed can be determined in various ways. It can be chosen to be upon depletion of the carbon source in the batch medium, as determined by on-line or off-line measurement of the carbon source concentration, or by an increase of the dissolved oxygen tension, which indicates depletion of the substrate. The time point for the start of the feed can further be chosen to correlate with a certain biomass value (as determined by on-line or off-line measurement of biomass) or according to a pre-defined time interval from the start of the fermentation.

In the method of the invention, supply of the culture with feed medium according to an exponential function can be achieved in various ways. In a preferred embodiment of the invention, the feeding rate is continuously calculated and controlled by the process control system of the fermenter, and the feeding rate is continuously increased following the exponential function. Thereby, the control of the mass flow of feed medium is controlled either via a mass flow meter (mass flow controller) or via a pump that supplies the medium according to the weight of the feed container measured by a balance.

In another embodiment of the invention, the feeding rate is semi-continuously increased by increasing it step-wise according to the exponential function. For instance, the volume or mass of feed medium may be re-calculated at given time intervals, e.g. every hour, and the new feeding rate is adjusted to the required value. Although the increase of the feeding rate is step-wise, the resulting profile of feeding is still exponential.

In yet another embodiment of the invention, the feeding rate is discontinuously increased. This can be achieved by calculation of the required amount of feed medium at a defined time point and the following pulse-wise addition of increasing amounts of the feed medium (either pre-defined or calculated, at selected time intervals, based on the current biomass). Although the cells are not continuously fed, this method still results in an exponential feeding profile leading to a constant specific growth rate.

In the method of the invention, any specific growth rate p that ensures growth and plasmid replication can be pre-defined for exponential feeding. The maximum and the optimum specific growth rate may depend on the particular host/plasmid combination and can be determined on a case-by-case basis for each host-plasmid system in experimental fed-batch or continuous (chemostat) fermentations. The specific growth rates suitable for fermentation of *E. coli* range between ca. 0.03 and ca. 1.5 h$^{-1}$. In a preferred embodiment of the invention, a low specific growth rate between ca. 0.05 and ca. 0.15 h$^{-1}$ is used, most preferably, the growth rate is ca. 0.1 h$^{-1}$. The advantage of lower specific growth rates is that the plasmid is allowed to replicate to a higher copy number, which results in a higher specific plasmid yield per biomass. Another advantage is that rom-negative pUC plasmids, which are preferred in the process of the invention, show elevated replication at low specific growth rates (Atlung et al., 1999). Most importantly, growth at low specific growth rates provokes the formation of tRNAs which are not charged with amino acids. Such uncharged tRNAs interact with the replication origin of the plasmid in a way that leads to enhanced replication activity.

In an embodiment of the invention, the feeding rate follows such exponential function throughout the entire feed phase.

According to another embodiment, the feed phase comprises a combination of an exponential phase and a phase wherein feeding is non-exponential. Examples for non-exponential feeding modes are linear or feedback-controlled feeding modes, e.g controlled by the pH value, by on-line measured cell density or by dissolved oxygen tension (DOT).

Preferably, non-exponential feeding is subsequent to exponential feeding.

In the embodiment of the invention that comprises both an exponential and a non-exponential feed phase, the overall feeding mode is such that more than ca. 20% of the total dry cell weight to be obtained in the feeding phase is generated during the exponential feeding phase. By way of example, if the specific growth rate in the exponential phase is high, i.e. the exponential function is steep, the proportion of the ultimately desired biomass (total dry cell weight), e.g. 50%, is achieved at an earlier point of time than when the feeding phase is run at a low specific growth rate.

In the case of a linear feeding mode, this mode can be linear constant, i.e. the flow rate of the feed is constant over time, or it can be linear increasing, i.e. the flow rate increases over time by a constant slope.

With this combined feeding mode, growth and plasmid formation are decoupled. During exponential feeding, a high amount of biomass is obtained (approximately 30 g dry cell weight per liter) within a short period of time. During linear feeding, accumulation of plasmid is due to a low specific growth rate. With this feed method, plasmid titers of 500-800 mg/L can be obtained.

End Point of Fermentation

The time point for termination of the fermentation can be freely chosen, depending on the specific needs of the manufacturer. Fermentations for plasmid production on a manufacturing scale usually take about 15 to 20 h. Plasmid replication during fermentation is highly dynamic, leading to a strong increase of the specific pDNA yield in the middle of fermentation time. Although not at maximum, the volumetric yield is high. When the purpose of the fermentation is to obtain biomass with the highest possible concentration of plasmid DNA, the fermentation can be terminated at this time point. This has striking advantages during the subsequent alkaline lysis and purification. The higher pDNA concentration in the biomass results in lower lysate volumes and shorter process times. Furthermore, the concentrations of pDNA in the process bulk liquids are higher. Beyond the point of maximum specific pDNA concentration, pDNA replication still occurs, leading to increasing pDNA concentration per L, but decreasing contents per g biomass. When the goal of the process is to obtain the highest possible total amount of plasmid DNA, fermentation may be extended until replication stops. Although not at maximum, the specific yield at this later phase of fermentation is still higher than in any of the methods known in the art.

This replication behavior provides a high degree of process flexibility, which allows to choose between a high specific or a high volumetric yield, simply dependent on fermentation time. No substantial decrease of the plasmid homogeneity is observed during the later phase of the fermentation.

Plasmid DNA obtained according to the method of the invention is recovered and purified according to known methods. Plasmid purification typically starts with the disintegration of the harvested cell mass, usually by alkaline lysis. Thereby, cells are subjected to high alkaline pH values together with detergents, so that the cells are lysed and the plasmids are released. Upon the following precipitation step with acetate buffer, proteins and genomic DNA get precipitated, whereas the plasmid DNA remains in the clarified supernatant. The subsequent purification steps comprise mainly filtration (ultrafiltration, diafiltration) and chromatographic techniques. The chromatographic methods may be selected from, for example, hydrophobic interaction, ion exchange or gel filtration chromatography.

Example 1

Fed-Batch Fermentation of *E. coli* JM108 Carrying the Plasmid pRZ-hMCP1

An exponential fed-batch fermentation was carried out in a 20 L scale fermenter (stirred tank reactor) with the *E. coli* K-12 strain JM108 harboring the plasmid pRZ-hMCP1. This plasmid (4.9 kb) is a derivative of pcDNA3™ (Invitrogen) containing a pUC ori and a kanamycin resistance marker. The gene of interest of pRZ-hMCP1 is monocyte chemoattractant protein 1 (Furutani et al., 1989) under the transcription control of the eukaryotic CMV (cytomegalo virus) promoter.

For a pre-culture, a glycerol stock of the strain (300 µL) was inoculated into a baffled 1000 mL shake flask containing 300 mL of a defined medium. This was cultivated in a rotary shaker at 300 rpm and 37° C. The pre-culture medium was composed as follows: $NH_4Cl$ 2 g/L, $MgSO_4 \cdot 7H_2O$ 0.24 g/L, glucose 10 g/L, L-proline 0.2 g/L, L-isoleucine 0.2 g/L, thiamine hydrochloride 1 mg/L, citric acid 2 g/L, $KH_2PO_4$ 5.44 g/L, $Na_2HPO_4 \cdot 12H_2O$ 14.38 g/L and trace element solution 16.7 mL/L. The trace element solution contained HCl (25%) 14.6 g/L, $CaCl_2 \cdot 2H_2O$ 0.44 g/L, $FeSO_4 \cdot 7H_2O$ 0.33 g/L, $CoCl_2 \cdot 6H_2O$ 0.14 g/L, $MnSO_4 \cdot H_2O$ 0.10 g/L, $CuSO_4 \cdot 5H_2O$ 15 mg/L and $ZnSO_4 \cdot 7H_2O$ 17 mg/L.

When the pre-culture had reached an optical density of approximately OD=1, it was transferred into the fermenter and the fermentation was started. The main culture batch medium contained the same components at the same concentrations as in the pre-culture. The fermenter contained 7 L of batch medium at the onset of the fermentation.

The temperature was controlled at 37° C. and the fermentation was operated with a back pressure of 0.35 bar. The fermenter was aerated with a process air mass flow rate of 1 vvm (volume air per volume medium and minute=7 L/min). When the dissolved oxygen tension dropped to 30%, it was maintained at this defined point by increasing the agitation rate of the stirrer (500-1000 rpm). In case the increase of the agitation rate was not sufficient to maintain the DO, the oxygen concentration of the air was enriched with pure oxygen. The pH was controlled at the set point of 7.0±0.2 with a solution of ammonium hydroxide (25%), which concomitantly served as source of nitrogen throughout the fermentation. If necessary, the pH was further controlled with 25% $H_2SO_4$.

Figure 1:
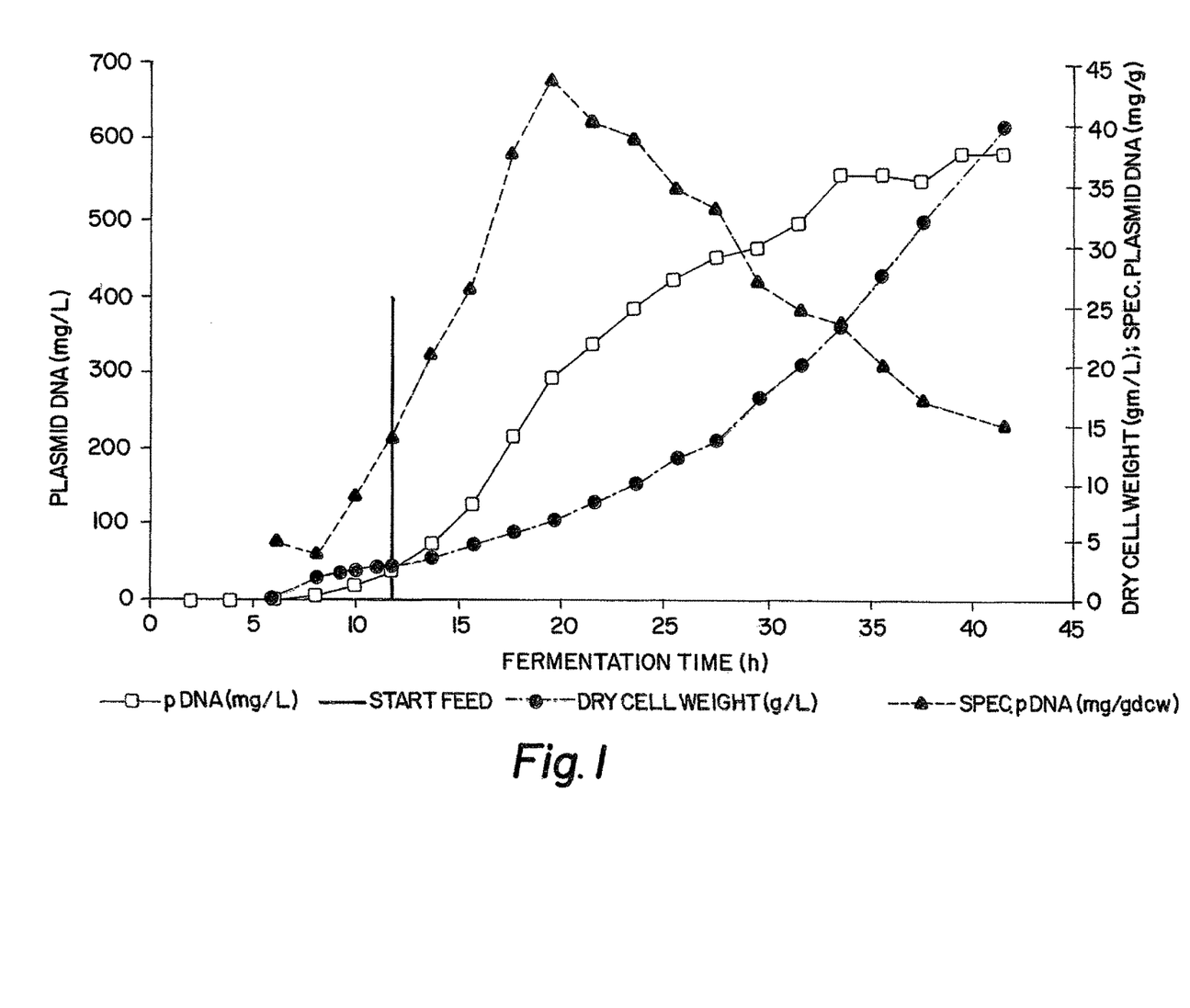
FIG. 1: Volumetric and specific pDNA yield and growth curve of a fed-batch fermentation of *E. coli* JM108

In FIG. 1, the volumetric and specific plasmid yield and the growth curve are shown. At the end of the fermentation, an exceptionally high volumetric pDNA yield of 590 mg/L was obtained. In addition, at 20 h of fermentation time, the specific pDNA yield reached a maximum of 44 mg pDNA per g dry cell weight, which is also an exceptionally high value. Towards the end of fermentation, the specific yield decreased to 15 mg/g DCW. This special course of specific and volumetric yield offers the advantage of several options as to which point of time the fermentation can be chosen to be terminated, dependent on the requirements of the manufacturing process. If biomass with the highest content of pDNA must be obtained, the fermentation can be terminated after 20 h, resulting in a volumetric yield of 300 mg/L. If the process goal is the highest volumetric yield, the fermentation can be prolonged beyond 40 h, which results in about 600 mg/L, but a lower specific yield.

Figure 2:
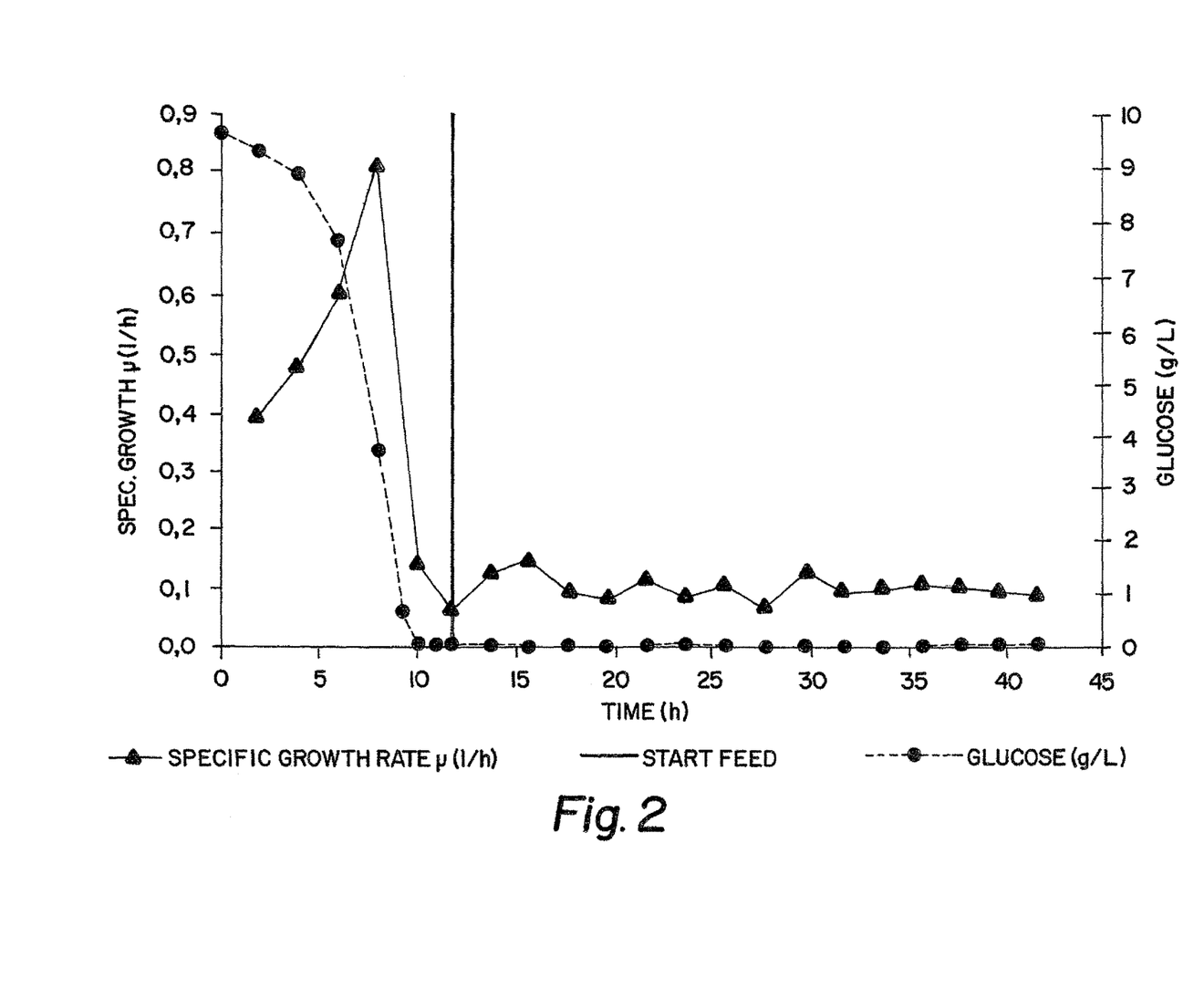
FIG. 2: Current specific growth rate of a fed-batch fermentation of *E. coli* JM108

After 10 h of batch cultivation, glucose in the batch medium was depleted (FIG. 2). This was determined with a rapid off-line measurement method (Yellow Springs Glucose Analyzer, YSI 2700 Select). The depletion of glucose served as the signal for the start of the exponential feeding phase. The feed medium was composed as follows: glucose 300 g/L; $MgSO_4*7H_2O$ 7.2 g/L; L-proline 6 g/L; L-isoleucine 6 g/L; thiamine hydrochloride 30 mg/L; citric acid 2 g/L; $KH_2PO_4$ 5.4 g/L; $Na_2HPO_4*12H_2O$ 14.4 g/L; $CaCl_2*2H_2O$ 220 mg/L; $FeSO_4*7H_2O$ 170 mg/L; $COCl_2*6H_2O$ 72 mg/L, $MnSO_4*H_2O$ 51 mg/L, $CuSO_4*5H_2O$ 8 mg/L and $ZnSO_4*7H_2O$ 9 mg/L.

Continuous exponential feeding was controlled via the process control system of the fermenter, based on biomass at the time of glucose depletion (estimated via optical density). The feeding rate was chosen to obtain a pre-defined specific growth rate p of 0.1 $h^{-1}$. The control of the feeding rate was accomplished by a mass flow meter. Throughout the entire fermentation, glucose was limiting, which was a prerequisite for exact growth rate control. Acetate, which would be a signal for glucose overflow, was not generated in significant amounts throughout most of the feeding phase (below 0.5 g/L until 40 h). As shown in FIG. 1, the biomass followed exactly the pre-defined exponential function. Beyond 40 h fermentation time, the predicted and actual biomass course deviated (not shown), and so the fermentation was terminated. FIG. 2 shows the current specific growth rate µ, which was calculated from the obtained dry cell weight, and which follows the pre-defined specific growth rate over most of the fermentation time.

Figure 3:
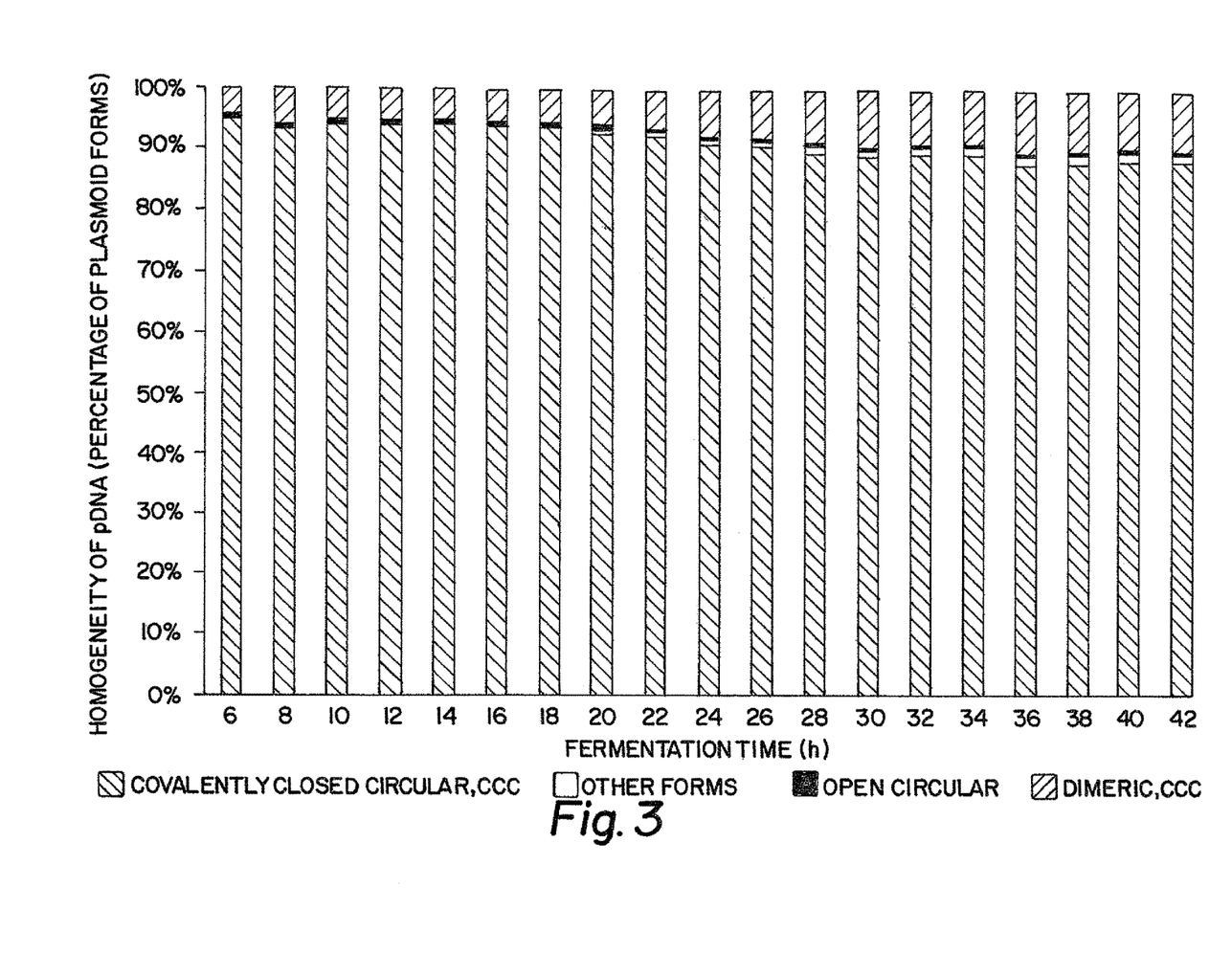
FIG. 3: Percentage of various plasmid forms over the time of a fed-batch fermentation of *E. coli* JM108
Figure 4:
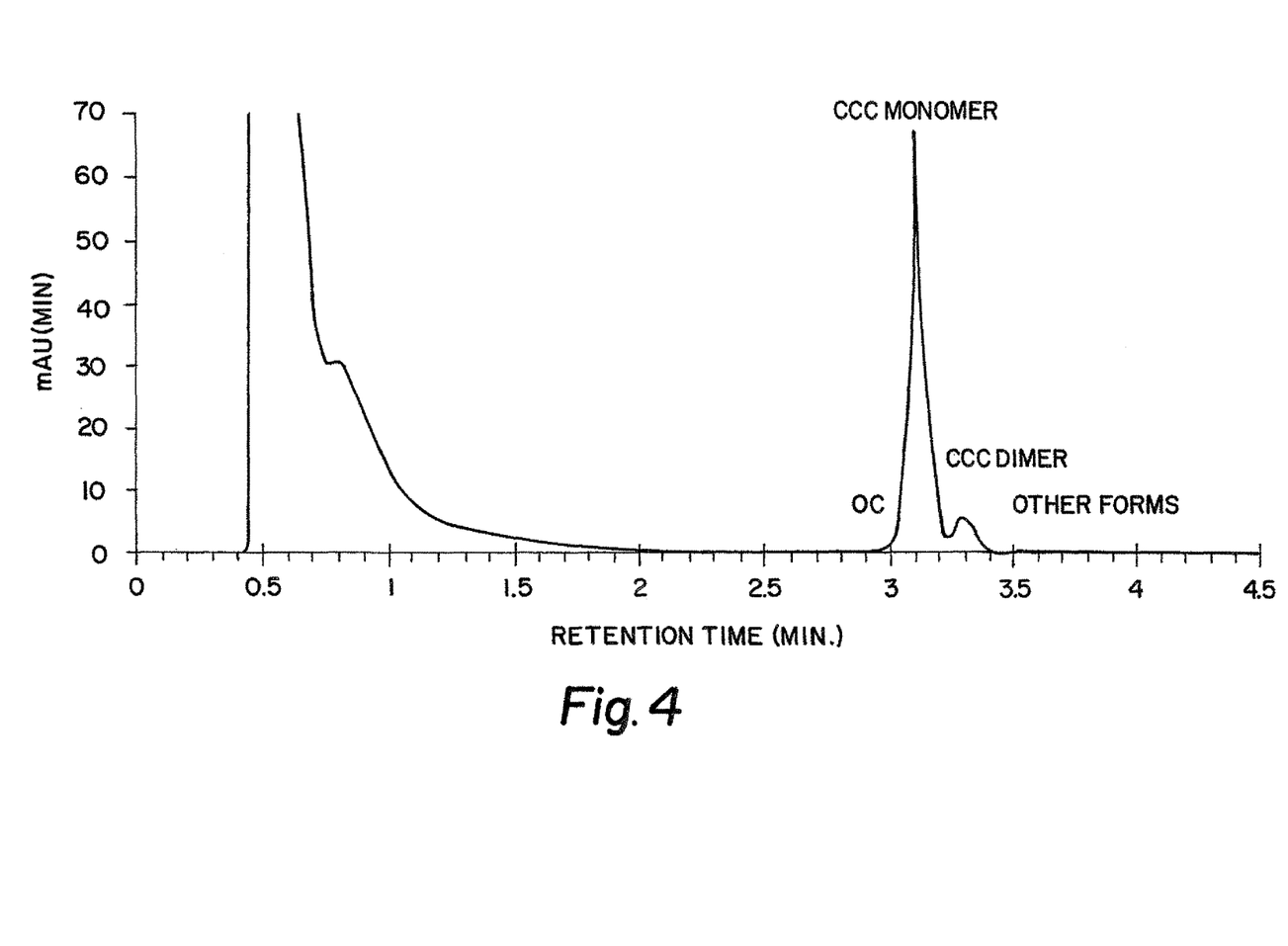
FIG. 4: Analytical chromatogram of the plasmid at the end of a fed-batch fermentation of *E. coli* JM108

FIG. 3 shows the percentage of the various plasmid forms over the fermentation time, analyzed with an anion exchange high performance liquid chromatography (AEX-HPLC) method. Throughout the major part of the fermentation, the percentage of covalently closed circular pDNA was above 90% and was maintained at minimum 89% until 42 hours of cultivation time. An analytical chromatogram of the plasmid at the end of the fermentation (42 h) is shown in FIG. 4.

This Example shows the excellent results of the invention in terms of volumetric and specific yield, accompanied with a high pDNA homogeneity.

Example 2

Influence of Isoleucine on the Plasmid Yield in an Exponential Fed-Batch Fermentation of *E. coli* JM108

In 1 L scale screening fermenters, the effect of isoleucine on growth and plasmid production was shown by applying the process described in Example 1. Two fermentations were carried out in the same way as described in Example 1, with the only difference that one medium contained isoleucine whereas the other medium did not. The remaining composition of the culture medium was identical as described in Example 1 as well as the cultivation conditions and the mode of exponential feeding at the growth rate of µ=0.1 $h^{-1}$. The feeding rate was automatically controlled via a balance and peristaltic pumps.

Figure 5:
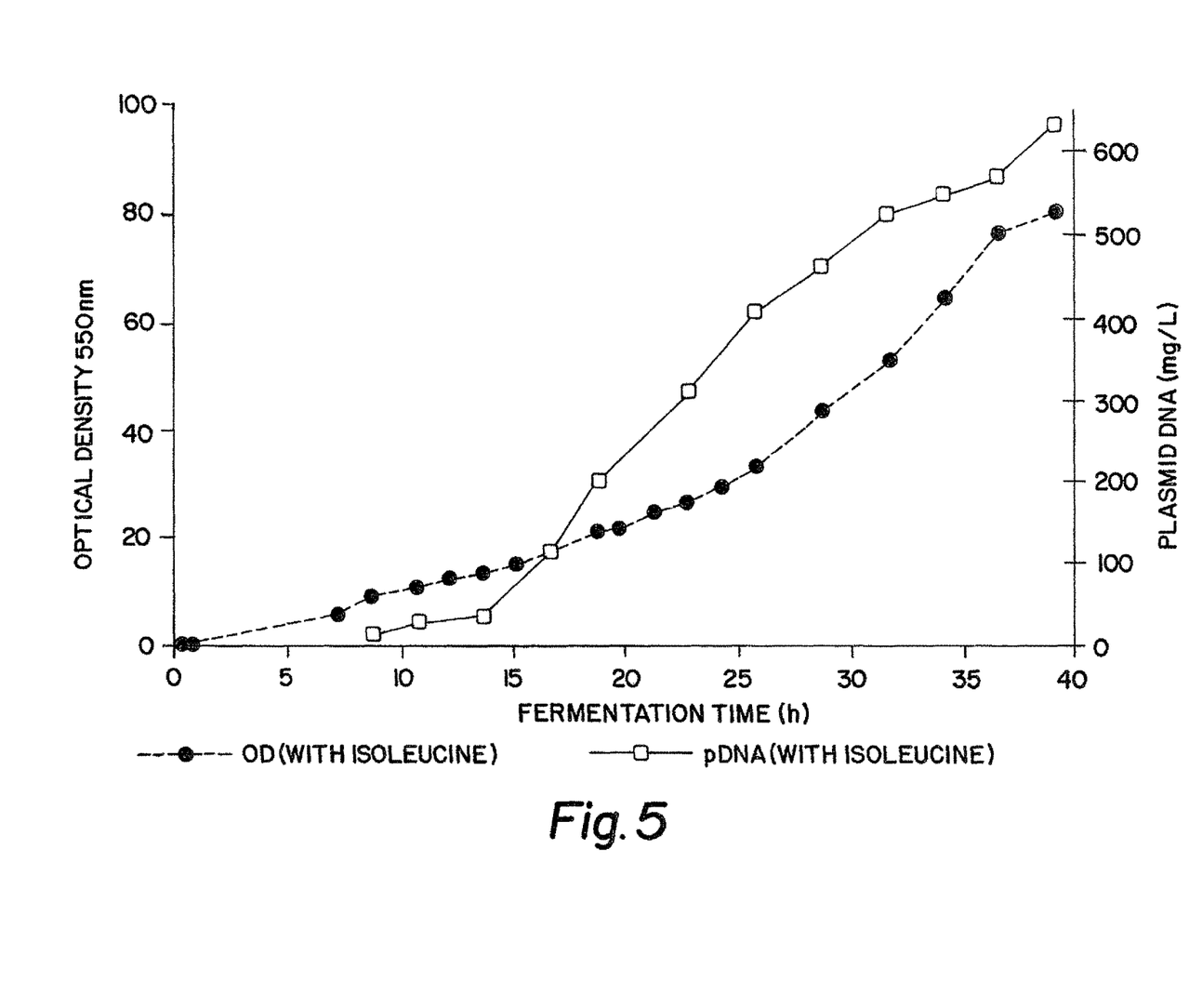
FIG. 5: Time course of the optical density and the volumetric pDNA yield of a fed-batch fermentation of *E. coli* JM108 in the presence of isoleucine
Figure 6:
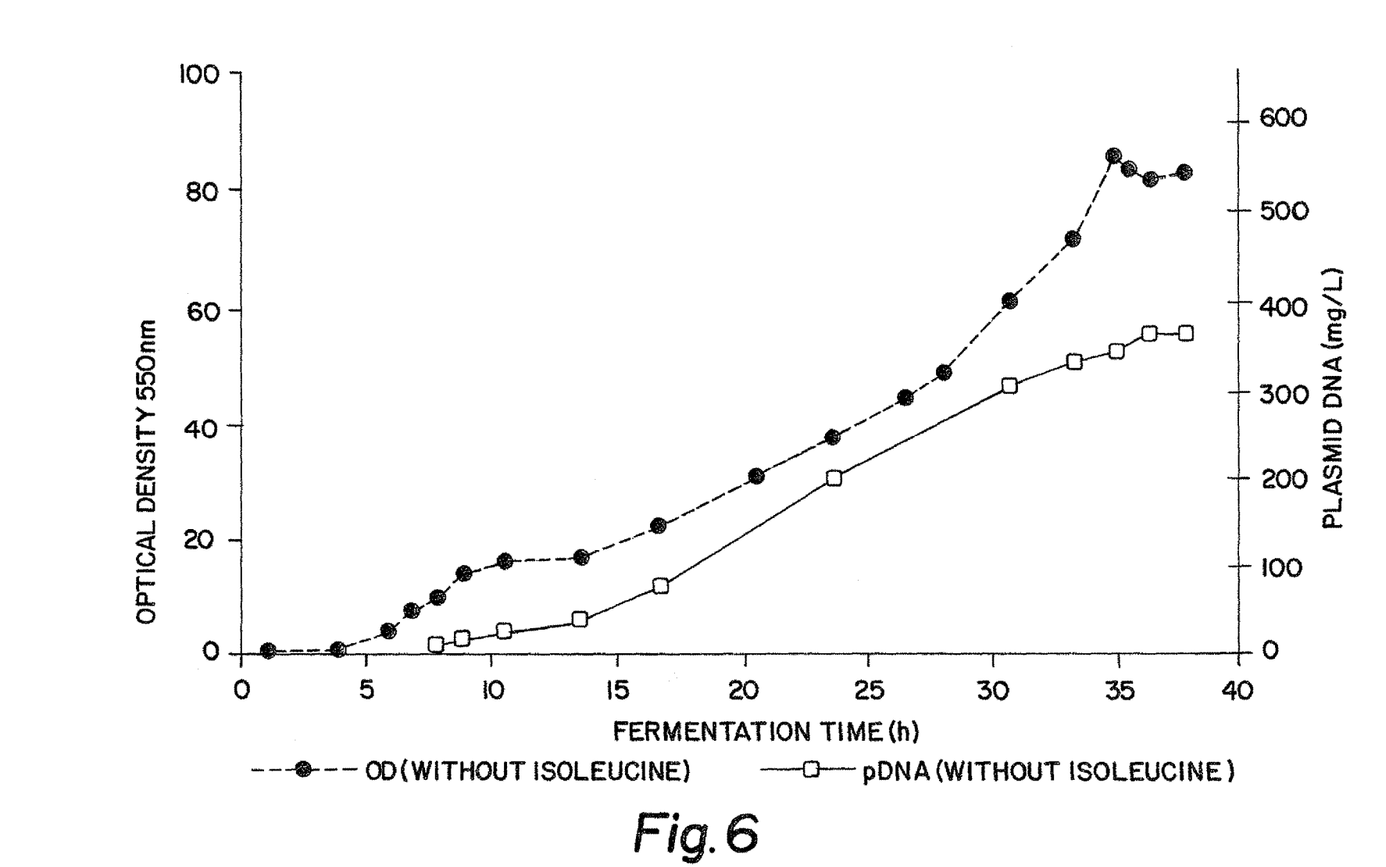
FIG. 6: Time course of the optical density and the volumetric pDNA yield of a fed-batch fermentation of *E. coli* JM108 in the absence of isoleucine

The time course of the optical density and the volumetric pDNA yield of both fermentations is shown in FIG. 5 (with isoleucine) and FIG. 6 (without isoleucine). Growth of both fermentations was nearly identical with an average specific growth rate of µ=0.09 $h^{-1}$ during the exponential feeding period. The volumetric pDNA yield was 633 mg/L with the medium containing isoleucine, whereas without isoleucine 398 mg/L were obtained. Table 1 gives a summary on the fermentation parameters. In both process variants the pDNA homogeneity was around 90% ccc. The maximum specific pDNA yield with isoleucine was more than twice as high as compared without isoleucine.

TABLE 1

Comparison of the characteristics of exponential fed-batch fermentations with and without the presence of isoleucine.

| Parameter | Unit | Medium with isoleucine | Medium without isoleucine |
| --- | --- | --- | --- |
| OD final | — | 81 | 87 |
| Dry cell weight final | g/L | 21.7 | 23.0 |
| Specific growth rate µ (average during feeding) | $h^{-1}$ | 0.09 | 0.09 |
| Volumetric pDNA yield (final) | mg/L | 633 | 398 |
| Specific pDNA yield (maximum) | mg/g DCW | 45 | 20 |
| Specific pDNA formation rate max ($q_p$) | mg/g DCW *h | 8.4 | 2.4 |
| Homogeneity of pDNA | % ccc form | 90 | 91 |

This Example demonstrates that the presence of isoleucine in the culture leads to higher volumetric and specific yields than obtained from cultures without isoleucine. However, even without isoleucine the pDNA yield of fermentations is still superior to known methods.

Example 3

Fed-Batch Fermentation of *E. coli* JM108 Carrying the Plasmid pRZ-hMCP1 (20 L Fermenter), Using an Exponential Feeding Algorithm, Succeeded by a Linear Feeding Mode In this Example, *E. coli* JM108 cells carrying the plasmid pRZ-hMCP1 are prepared and cultivated as described in Example 1. Other than in Example 1, the feeding phase is divided into two different parts:

(1) an exponential feeding phase, where the feeding rate follows an exponential feeding function in order to maintain a specific growth rate of µ=0.25 $h^{-1}$, and
(2) a linear constant feeding phase, where the feeding rate is maintained at a constant value of 200 mL/h.

The time point, when switching from exponential to linear feeding takes place, is after 10 hours of exponential feeding. The linear feeding phase is chosen to be 10 hours. By such fermentation, volumetric and specific plasmid yields are obtained that range from 500 to 800 mg pDNA/L or 20 to 30 mg pDNA/g DCW.

REFERENCES

Andersen, D. C., Swartz, J., Ryll, T., Lin, N., and Snedecor, B. (2001) Metabolic oscillations in an *E. coli* Fermentation. Biotech. Bioeng. 75:2, 212-218.

Atlung, T., Christensen, B. B., and Hansen, F. G. (1999). Role of the Rom protein in copy number control of plasmid pBR322 at different growth rates in *Escherichia coli* K-12. Plasmid 41, 110-119.

CBER, Center for Biologics Evaluation and Research, U.S. Food and Drug Administration, Rockville, Md. (1998). Guidance for industry—guidance for human somatic cell therapy and gene therapy.

Chen, W., Graham, C., and Ciccarelli, R. B. (1997). Automated fed-batch fermentation with feed-back controls based on dissolved oxygen (DO) and pH for production of DNA vaccines. J. Ind. Microbiol. Biotechnol., 18, 43-48.

Furutani Y., Nomura H., Notake M., Oyamada Y., Fukui T., Yamada M., Larsen C. G., Oppenheim J. J. and Matsushima K. (1989). Cloning and sequencing of the cDNA for human monocyte chemotactic factor (MCAF).

Biochem Biophys Res Commun 159(1), 249-55. Hofmann, K. H., Neubauer, P., Riethdorf, S., and Hecker, M. (1989). Amplification of pBR322 plasmid DNA in *Escherichia coli* relA strains during batch and fed-batch fermentation. J. Basic Microbiol. 30, 37-41.

Lahijani, R., Hulley, G., Soriano, G., Horn, N. A., and Marquet, M. (1996). High-yield production of pBR322-derived plasmids intended for human gene therapy by employing a temperature-controllable point mutation. Hum. Gene Ther. 7, 1971-1980.

Lawther, R. P., Calhoun, D. H., Adams, C. W., Hauser, C. A., Gray, J., and Hatfield, G. W. (1981). Molecular basis of valine resistance in *Escherichia coli* K-12. Proc. Natl. Acad. Sci. USA 78:2, 922-925.

O'Kennedy, R. D., Baldwin, C., and Keshavarz-Moore, E., (2000). Effects of growth medium selection on plasmid DNA production and initial processing steps. J. Biotechnol. 76, 175-183.

O'Kennedy et al (2003). Effects of fermentation strategy on the characteristics of plasmid DNA production. Biotechnol Appl. Biochem. 34, 83-90.

Reinikainen, P., Korpela, K., Nissinen, V., Olkku, J., Soderlund, H., and Markkanen, P. (1988). *Escherichia coli* plasmid production in Fermenter. Biotech. Bioeng. 33, 386-393.

Sambrook, J., and Russel, D. W. (2001). *Molecular Cloning—a Laboratory Manual*, 3$^{rd}$ ed., J. Argentine, N. Irwin, K. A. Janssen, S. Curtis, M. Zierler, et. al., eds. (Cold Spring Harbor, N.Y.).

Schoenfeld, T., Mendez, J., Storts, D. R., Portman, E., Patterson, B., Frederiksen, J., and Smith, C. (1995). Effects of bacterial strains carrying the endA1 genotype on DNA quality isolated with Wizard Plasmid Purification System. Promega Notes, 53, 12-22.

Ulmer, J. B., Donelly, J. J., and Liu, M. A. (1996). Toward the development of DNA vaccines. Curr. Opin. Biotechnol. 7, 653-658.

Vieira, I. and Messing, I. 81982). The pUC plasmids, an M133 mp7-derived system for insertion mutagenesis and sequencing with synthetic universal primers. Gene 19, 259-268.

Wang et al. (2001). Medium design for Plasmid DNA based on stoichimetric model. Proc. Biochem. 36, 1085-1093.

Wrobel, B. and Wegrzyn, G. (1998). Replication regulation of ColE1-like plasmids in amino ascid-starved *Escherichia coli*. Plasmid 39, 48-62.

Yanisch-Perron, C., Vieira, J., and Messing, J. (1985). Improved M13 phage cloning vectors and host strains: nucleotide sequences of the M13 mp18 and pUC19 vectors. Gene 33, 103-119.

Zhang and Greasham (1999). Chemically defined media for commercial fermentations. Appl. Microbiol. Biotechnol. 51, 407-421.

The invention claimed is:

1. A process for producing plasmid DNA on a manufacturing scale, said process comprised of the steps of:
   a) growing *E. coli* cells that bear a plasmid carrying a gene of interest in a pre-culture and subsequently fermenting in a main culture, wherein the *E. coli* cells are from *E. coli* K-12 strain JM108 or a derivative thereof;
   b) recovering and purifying the plasmid DNA from the main culture;
   wherein the main culture is subjected to a fed-batch process comprising a batch phase and a feeding phase, wherein the batch phase and the feeding phase each comprises a chemically defined culture medium comprising a growth-limiting substrate, and wherein the feeding phase commences after the batch phase and wherein the culture medium of the feeding phase is added at a feeding rate ($F_t$) that follows, for at least a fraction of the feeding phase, the pre-defined exponential function of $$F_t = \frac{\mu * X_0}{Y_{X/S} * C_S} * e^{\mu t}, \text{ wherein}$$

$F_t$ is the flow rate [L/h] of the feed medium;
   $X_0$ is the total amount of biomass dry cell weight [g] at start of the feeding phase;
   $Y_{X/S}$ is the biomass yield coefficient (g dry cell weight per g substrate);
   $C_S$ is the concentration of said substrate in said feed medium [g/L];
   $\mu$ is the specific growth rate [h$^{-1}$]; and
   t is the time interval [h] from start of the feeding phase, and
   wherein said fraction of said feeding phase during which said feeding rate follows said exponential function is such that a constant specific growth rate ranging from 0.03 to 1.5 h$^{-1}$ is achieved over the entire fraction of the feeding phase.

2. The process of claim 1, wherein said preculture medium is chemically defined.

3. The process of claim 1, wherein the plasmid has a ColE1-type origin of replication.

4. The process of claim 3, wherein the plasmid is a pUC plasmid.

5. The process of claim 1, wherein a specific plasmid DNA yield of about 20 to about 45 mg/g DCW is obtained.

6. The process of claim 1, wherein the feeding rate is increased by continuously adding the medium following said exponential function.

7. The process of claim 1, wherein the feeding rate is increased in a semi-continuous mode by adding the medium step-wise following said exponential function.

8. The process of claim 1, wherein the feeding rate is increased in a discontinuous mode by adding the medium pulse-wise following said exponential function.

9. The process of claim 1, wherein the exponential function of the feeding rate is based on measurements of the amount of biomass.

10. The process of claim 1, wherein the growth limiting substrate is a carbon source.

11. The process of claim 10, wherein said carbon source is glucose.

12. The process of claim 1, wherein the growth rate is about 0.03 to about 0.2 h$^{-1}$.

13. The process of claim 1, wherein the medium of the batch culture at the start of fermentation is comprised of ammonium salts as the nitrogen source.

14. The process of claim 13, wherein the ammonium salt is ammonium chloride.

15. The method of claim 1, wherein the pH value of the main culture is adjusted by addition of ammonium hydroxide.

16. The process of claim 1, wherein said culture media are free of antibiotics.

17. The process of claim 16, wherein the culture media used in the pre-culture is free of antibiotics.

18. The process of claim 1, wherein said culture medium of said batch phase and said feeding phase is comprised of
   a) an organic carbon source selected from glucose, glycerol, fructose, lactose, sucrose, arabinose, or a mixture thereof;
   b) an anorganic nitrogen source selected from ammonium salts and ammonium hydroxide, wherein the nitrogen source is present as a component of the medium or added to the medium during fermentation;
   c) inorganic salts; and
   d) isoleucine.

19. The process of claim 18, wherein said culture medium further comprises one or more substances that complement an auxotrophy of the *E. coli* strain.

20. The process of claim 18, wherein said culture medium is a batch medium present at the start of a batch fermentation or at the start of the batch phase of a fed-batch fermentation and is comprised of:
   a) glucose in concentration of about 10 to about 30 g/L;
   b) an ammonium salt or ammonium hydroxide in a concentration such that the ammonium concentration is about 0.5 to about 2 g/L;
   c) inorganic ions that serve as a supply with macro and micro elements; and
   d) isoleucine in a concentration of about 0.1 to about 0.3 g/L.

21. The process of claim 20, wherein said culture medium further comprises one or more substances that complement an auxotrophy of the *E. coli* strain.

22. The process of claim 18, wherein said culture medium is a feed medium that is added during the feeding phase of a fed-batch fermentation and is comprised of:
   a) glucose in concentration of about 300 to about 500 g/L;
   b) inorganic ions that serve to supply with macro and micro elements; and
   c) isoleucine in a concentration of about 6 g/L.

23. The process of claim 22, wherein said culture medium further comprises one or more substances that complement an auxotrophy of the *E. coli* strain.

24. The process of claim 1, wherein the medium of the feeding phase comprises isoleucine and wherein said isoleucine increases the yield of plasmid DNA in said process as compared to when the medium of the feeding phase does not comprise isoleucine.

25. The process of claim 24, wherein the medium of the batch culture comprises isoleucine in a concentration of about 0.05 to about 2 g/L.

26. The process of claim 1, wherein said fraction of said feeding phase during which said feeding rate follows said exponential function is such that more than about 20% of the total dry cell weight that is obtained in the feeding phase is generated during said fraction.

* * * * *